United States Patent
Segura-Orsoni et al.

(10) Patent No.: US 8,287,891 B2
(45) Date of Patent: Oct. 16, 2012

(54) INVERSE EMULSIONS COMPRISING AVERMECTINS AND COSMETIC/DERMATOLOGICAL APPLICATIONS THEREOF

(75) Inventors: Sandrine Segura-Orsoni, Mandelieu (FR); Fanny Diaz-Astruc, Houston, TX (US)

(73) Assignee: Galderma S.A., Cham (CH)

( * ) Notice: Subject to any disclaimer, the term of this patent is extended or adjusted under 35 U.S.C. 154(b) by 0 days.

(21) Appl. No.: 12/213,554

(22) Filed: Jun. 20, 2008

(65) Prior Publication Data

US 2009/0035338 A1 Feb. 5, 2009

Related U.S. Application Data

(63) Continuation of application No. PCT/FR2006/051378, filed on Dec. 18, 2006.

(30) Foreign Application Priority Data

Dec. 20, 2005 (FR) ..................................... 05 12956

(51) Int. Cl.
*A61K 9/00* (2006.01)
*A61K 8/02* (2006.01)

(52) U.S. Cl. ........................................ 424/401; 424/400

(58) Field of Classification Search ................... 424/401
See application file for complete search history.

(56) References Cited

U.S. PATENT DOCUMENTS

| | | | |
|---|---|---|---|
| 4,389,397 A | 6/1983 | Lo et al. | |
| 5,952,372 A | 9/1999 | McDaniel | |
| 6,133,310 A | 10/2000 | Parks | |
| 6,319,945 B1 | 11/2001 | Parks | |
| 6,399,651 B1 | 6/2002 | Parks | |
| 6,399,652 B1 | 6/2002 | Parks | |
| 6,433,006 B2 | 8/2002 | Parks | |
| 7,897,559 B2 | 3/2011 | Parks | |
| 2002/0019354 A1 | 2/2002 | Parks | |
| 2002/0035076 A1 | 3/2002 | Parks | |
| 2002/0061855 A1 | 5/2002 | Parks | |
| 2002/0156029 A1 | 10/2002 | Parks | |
| 2003/0064940 A1 | 4/2003 | Parks | |
| 2003/0180350 A1 | 9/2003 | Razzak et al. | |
| 2004/0167084 A1 | 8/2004 | Parks | |
| 2006/0100165 A1 | 5/2006 | Manetta et al. | |
| 2007/0116731 A1 | 5/2007 | Astruc et al. | |

FOREIGN PATENT DOCUMENTS

| | | |
|---|---|---|
| EP | 0 045 655 A2 | 2/1982 |
| WO | 2004093886 A1 * | 11/2004 |
| WO | WO2004/093886 A1 | 11/2004 |
| WO | WO 2004093886 A1 * | 11/2004 |
| WO | WO2005/089806 A1 | 9/2005 |

OTHER PUBLICATIONS

The American Academy of Dermatology, Rosacea, 1987-2009, Intendis, 930 E. Woodfield Road, P.O. Box 4014, Schaumburg, IL 60168-4014, printed pp. 1-6.*
International Search Report PCT/FR2006/051378 dated May 7, 2007.

* cited by examiner

*Primary Examiner* — Sreeni Padmanabhan
*Assistant Examiner* — Timothy E Betton
(74) *Attorney, Agent, or Firm* — SNR Denton US LLP

(57) ABSTRACT

Physically and chemically stable, oxidation-resistant, cosmetic/dermatological inverse emulsions contain a therapeutically effective amount of at least one avermectin compound, notably ivermectin, a glycolic or aqueous/glycolic dispersed hydrophilic phase, a continuous lipophilic phase and an emulsifier having an HLB ranging from 2 and 7, and are useful for the treatment of a variety of dermatological conditions/afflictions, e.g., rosacea.

15 Claims, No Drawings

INVERSE EMULSIONS COMPRISING AVERMECTINS AND COSMETIC/DERMATOLOGICAL APPLICATIONS THEREOF

CROSS-REFERENCE TO PRIORITY/PCT APPLICATIONS

This application claims priority under 35 U.S.C. §119 of FR 00512956, filed Dec. 20, 2005, and is a continuation of PCT/FR 2006/051378, filed Dec. 18, 2006 and designating the United States (published in the French language on Jun. 28, 2007 as WO 2007/071876 A1; the title and abstract were also published in English), each hereby expressly incorporated by reference in its entirety and each assigned to the assignee hereof.

BACKGROUND OF THE INVENTION

1. Technical Field of the Invention

The present invention relates to novel compositions of inverse emulsion type comprising at least one compound from the family of the avermectins, preferably ivermectin, and topical pharmaceutical compositions comprised thereof for the treatment of rosacea.

2. Description of Background and/or Related and/or Prior Art

Ivermectin is a mixture of two compounds belonging to the class of the avermectins, 5-O-demethyl-22,23-dihydroavermectin $A_{1a}$ and 5-O-demethyl-22,23-dihydroavermectin $A_{1b}$. They are also known under the trademarks of 22,23-dihydroavermectin $B_{1a}$ and 22,23-dihydroavermectin $B_{1b}$. Ivermectin comprises at least 80% of 22,23-dihydroavermectin $B_{1a}$ and less than 20% of 22,23-dihydroavermectin $B_{1b}$. This active agent forms part of the class of the avermectins, a group of macrocyclic lactones produced by the bacterium *Streptomyces avermitilis* (Reynolds J. E. F. (Ed), (1993) Martindale, *The Extra Pharmacopoeia*, 29th Edition, Pharmaceutical Press, London).

In the middle of the 1980s, ivermectin was presented as a broad-spectrum anti-parasitic medicament for veterinary use (Campbell W. C. et al. (1983), "Ivermectin: a potent new anti-parasitic agent," *Science*, 221, 823-828). It is effective against the majority of common intestinal worms (except for the Teniae), the majority of the acarids and a few lice. It exhibits in particular a high affinity for the glutamate-dependent chloride channels present in the nerve and muscle cells of invertebrates. Its attachment to these channels promotes an increase in the membrane permeability to chloride ions, resulting in hyperpolarization of the nerve or muscle cell. This results in neuromuscular paralysis, which can bring about the death of certain parasites. Ivermectin also interacts with other ligand-dependent chloride channels, such as those involving the GABA (γ-aminobutyric acid) neuromediator.

Ivermectin is more particularly an anthelmintic. It has been described in man in the treatment of onchocerciasis due to Onchocerca volvulus, of gastrointestinal strongyloidiasis (anguillulosis) (product Stromectol®) and of human scabies (Meinking T. L. et al., *N. Enql. J. Med.*, 1995, Jul., 6, 333(1), 26-30, The treatment of scabies with ivermectin) and in the treatment of microfilaremia diagnosed or suspected in subjects affected by lymphatic filariasis due to *Wuchereria bancrofti*.

U.S. Pat. No. 6,133,310 describes the administration of ivermectin topically, in the form of a prototype of a lotion constituted of a mixture of ivermectin and of water, and also mentions the possibility of a prototype of a cream constituted, for its part, of the mixture of ivermectin and of an excipient, such as propylene glycol or sodium lauryl sulfate, but does not describe any pharmaceutical composition as such. These mixtures are similar to experimental preparations employed in the context of first results of a proof of concept. Specifically, the disclosure in this patent does not teach one skilled in the art anything regarding the feasibility of industrially acceptable pharmaceutical compositions comprising ivermectin, in particular having a good cosmetic quality and a lifetime sufficient for an industrial pharmaceutical product (minimum 2 years).

The ivermectin according to the present invention comprises at least 80% of 22,23-dihydroavermectin $B_{1a}$ and less than 20% of 22,23-dihydroavermectin $B_{1b}$.

Ivermectin is highly unstable in the presence of water and it proves to be particularly difficult to obtain stable pharmaceutical compositions comprising ivermectin. It exhibits the difficulty of being very sparingly soluble and rarely stable in the cosmetic or pharmaceutical solvents commonly employed, in particular water; specifically, it is sensitive to an aqueous environment. This sensitivity to water can result in chemical instability of the active principle and/or in crystallization of the initially dissolved active principle. This sensitivity to water thus limits its formulation in cosmetic or dermatological compositions administered via the topical or oral route.

The phenomena of chemical decomposition and/or of crystallization of ivermectin in the presence of water have as consequences a reduction in or loss of effectiveness and uncertainty with regard to the dose of active principle employed during the administration thereof, which militates against the desired objective. In addition, this decomposition of the active principle and/or its crystallization can modify the overall stability of the compositions and their appearance.

The pharmaceutical dosage form most commonly employed today in dermatology is the oil-in-water emulsion in which the active principle is preferably dissolved in the lipophilic phase. However, this solution remains rather unsatisfactory as, in order to meet an objective of concentration of active principle having a therapeutically quantifiable effectiveness, very high concentrations of solvating oils will be necessary, resulting in products which would without doubt be rather unpleasant to use, due to their sticky feel, and physically unstable, while remaining limited in concentration of active principle.

One possibility is to dissolve the active principle in the hydrophilic phase of the emulsion, within the limit of its solubility in aqueous or aqueous/glycolic media.

However, this solution does not make it possible to solve the problems of chemical stability encountered with ivermectin as the activity in water of the emulsion remains very high.

The replacement of all or part of the aqueous phase by one or more glycols generally results in formulations which are not very acceptable cosmetically. In particular, above 20% glycol, the formulation is not very acceptable cosmetically due to its sticky feel, and it is often not guaranteed to be physically stable.

SUMMARY OF THE INVENTION

It has now surprisingly been found that a significant portion of the aqueous phase can be replaced by glycols without, however, encountering the abovementioned disadvantages and drawbacks.

The assignee hereof has already described, in FR-2,867, 684, pharmaceutical compositions comprising ivermectin, but it remains important to further improve the stability of compositions comprising ivermectin while retaining the tolerance thereof.

Indeed, it has now surprisingly been found that compositions of inverse emulsion type according to the invention exhibit very good physical and chemical stability and very good tolerance on the skin. Specifically, it transpires that it is particularly suitable for the treatment of dermatological conditions and more particularly highly suitable for the treatment of rosacea.

The present invention also features a process for formulating the subject compositions and the preparation therefrom of topical medicaments useful for the treatment of rosacea.

The preparation of an inverse emulsion as an alternative was not obvious to one skilled in the art due to the known difficulties in formulating ivermectin in stable compositions. The term "inverse emulsion" means an emulsion of hydrophilic phase dispersed in lipophilic phase type.

The use of hydrophilic solubilizing agents, such as propylene glycol, was also not apparent to one skilled in the art due to the fact that the high concentrations necessary were not favorable to good physical stability of the formulation and to an acceptable cosmetic feel.

It was also not obvious that good tolerance would be obtained with solubilizers, such as propylene glycol, as phenomena of skin intolerance have been shown in man, for example in individuals who are healthy (Motoyoshi et al., *Cosmet. and Toiletries*, 99, 83-89, 1984).

Thus, need existed for compositions which made it possible to correspond to one or more of the following aspects: to have good stability of the formulation under cold conditions and under hot conditions, in particular with regard to the maintenance of the size of the globules and to the absence of phase separation, and a stable viscosity over time, to have good resistance of the ivermectin with respect to oxidation phenomena, to make possible good chemical stability of the active principle and good availability of the latter for the skin, and to exhibit good skin tolerance. It was also desirable to be able to have available compositions which allow a high dispersed fraction by volume. Furthermore, it was desirable for the preparation of such compositions to benefit from an advantageous method of preparation.

Indeed, formulations of glycol-in-oil type have now surprisingly been developed which make it possible to solve the various problems related to the aspects mentioned above while making it possible, in particular, to provide good physical stability of the composition as is but also to make possible good chemical stability and availability of the active principle, in particular ivermectin, present therein. The compositions according to the invention also have the advantage of exhibiting good skin tolerance and of allowing a high dispersed fraction by volume.

The present invention thus features compositions comprising at least one compound of the family of the avermectins, preferably ivermectin, wherein such compositions are inverse emulsions comprising a glycolic or aqueous/glycolic dispersed hydrophilic phase, a continuous lipophilic phase and an emulsifier with an HLB of from 2 and 7, said compositions not comprising DHEA and/or its precursors and/or chemical and/or biological derivatives and/or vitamin D derivatives.

DETAILED DESCRIPTION OF BEST MODE AND SPECIFIC/PREFERRED EMBODIMENTS OF THE INVENTION

The compounds of the family of the avermectins according to the present invention include, in particular, invermectin, ivermectin, avermectin, abamectin, doramectin, eprinomectin and selamectin. Preferably, the compound of the family of the avermectins is ivermectin.

The compositions according to the invention preferably comprise solely the compound of the family of the avermectins, preferably ivermectin, as active principle.

The term "HLB" means the "Hydrophilic/Lipophilic Balance", which corresponds to the equilibrium from the size and the strength of the hydrophilic group and the size and the strength of the lipophilic group of the emulsifier.

The compositions according to the invention makes it possible to provide good properties of release/penetration of the active principle, in particular ivermectin, in the various layers of the skin, resulting in good availability of the active principle in the skin, the active principle being present in the dissolved state.

The term "dissolved form" means a dispersion of the active principle in the molecular state in a liquid, no crystallization of the active principle being visible to the naked eye or even using a cross-polarization optical microscope.

The formulation of the ivermectin, dissolved in a glycolic or aqueous/glycolic phase, in inverse emulsions according to the invention thus makes it possible, surprisingly, to solve the problems of chemical stability and of crystallization commonly encountered when formulating with this type of active principle.

The present invention also features the preparation of inverse emulsions, comprising a glycolic or aqueous/glycolic hydrophilic phase, which are completely stable chemically and physically, even with a high dispersed fraction by volume, which show no chemical decomposition and/or crystallization of the ivermectin and which are particularly well tolerated.

The term "physical stability" according to the invention means a composition which does not exhibit any alteration in macroscopic appearance (phase separation, change in color of appearance, viscosity, and the like) or microscopic appearance (recrystallization of the active principles) after storing at the temperatures of 4° C., 25° C., 40° C. and 55° C. for 3 months.

The term "chemical stability" according to the invention means a composition in which the content of active principle remains stable after three months at ambient temperature and at 40° C. A stable content of active principle means, according to the invention, that the content exhibits very little variation with respect to the initial content, namely, that the variation in content of active principle at the time T should not be less than 90% to more particularly than 95% of the initial content at T0.

Preferably, the compound of the family of the avermectins, preferably ivermectin, is dissolved in the glycolic or aqueous/glycolic dispersed phase of the inverse emulsion according to the invention. More advantageously, the compound of the family of the avermectins, in particular ivermectin, is dissolved exclusively in the glycol(s) included in the inverse emulsion according to the invention.

The compositions according to the invention are preferably suitable for topical application on the skin, superficial body growths and/or mucous membranes. Same generally comprise a physiologically acceptable medium and an amount of compound of the family of the avermectins, in particular ivermectin, sufficient to produce the desired effect. The proportion by weight of the compound of the family of the avermectins, preferably ivermectin, with respect to the total weight of the composition, can thus range from 0.001% to 20% by weight, with respect to the total weight of the composition, preferably from 0.01 and 5% by weight, in particular from 0.02 to 2% by weight. More particularly, the subject compositions comprise 1% by weight of active principle, in particular ivermectin, with respect to the total weight of the composition.

The glycols according to the present invention can be defined as alkylene or polyalkylene glycols. Exemplary thereof are $(C_1-C_6)$alkylene and poly$(C_1-C_6)$alkylene glycols, such as ethylene glycol, polyethylene glycol (2 to 20 monomers), propylene glycol, dipropylene glycol, butylene glycol, pentylene glycol or hexylene glycol. They may or may not be oxyethylenated (2 to 50 EO). Those preferred according to the invention are hexylene glycol, propylene glycol and dipropylene glycol, and polyethylene glycol 400 (PEG 400).

The glycols according to the invention will advantageously have, as solubility parameter, a $\delta p$ of less than 10, it being understood that the 3 Hansen solubility parameters: $\delta d$, $\delta p$ and $\delta h$, characterize, for a given constituent, the energies corresponding respectively to the dispersive interactions, the polar interactions and the interactions of hydrogen bond type existing from the molecules of this constituent, $\delta p$ characterizing more particularly the forces of Debye interactions from dipoles and being a function of the number of oxygen atoms in the formula of the given constituent (S. Paint Technology, 30, 195, 1967, "The three-dimensional solubility parameter—Key to paint component affinities"). Preferably, the solubility parameters of the glycols which are preferred according to the invention are from 5 and 10.

Preferably, the dispersed hydrophilic phase comprises at least one glycol selected from propylene glycol, hexylene glycol, dipropylene glycol and PEG 400.

Exemplary are lipophilic compounds which can be used to form the continuous fatty phase of the emulsions according to the invention, of mineral oils (liquid paraffin), oils of vegetable origin (avocado oil, sweet almond oil, soybean oil), oils of animal origin (lanolin), synthetic oils (perhydrosqualene), silicone oils (cyclomethicone, dimethicone) and fluorinated oils (perfluoropolyethers). Use may also be made of fatty alcohols, such as cetyl alcohol, Guerbet alcohols, in particular octyldodecanol, marketed under the trademark Eutanol G, fatty acids, waxes, gums and in particular silicone gums.

The fatty phase can also be constituted of linear or branched mono-, di- or triesters of synthetic origin, in particular isopropyl myristate, isopropyl palmitate or caprylic/capric triglyceride (Miglyol 812).

Preferably, non-oxidizable compounds are employed in order to constitute the oils of the continuous lipophilic phase, which are preferably selected from those of silicone type, those of ester type or those of mineral type.

The compounds participating in the composition of the lipophilic phase of the emulsion will have, as Hansen solubility parameter, a $\delta p$ of less than 5 and, for example, from 0 and 2.

Moreover, in order to avoid any crystallization of the ivermectin, the overall solubility parameter of the lipophilic phase: $\delta t_1 = \sqrt{\delta d + \delta p + \delta h}$, will have a value of less than 18, for example from 10 and 18 and preferably from 12 and 18.

The fraction by volume of the dispersed hydrophilic phase in the emulsion according to the invention ranges from 10 to 90%, with respect to the total volume of the emulsion. It can be exclusively glycolic or aqueous/glycolic.

The proportion by volume of glycols, with respect to the total volume of the dispersed hydrophilic phase, ranges from 30% to 100% to preferably from 60% to 100%.

Emulsifiers (or surfactants) are natural or synthetic substances formed of a hydrophilic or polar moiety and of a lipophilic or non-polar moiety. These are amphiphilic molecules since they have a twofold polarity. Emulsifiers are characterized by their HLB; if the HLB is high, the hydrophilic part is predominant, if the HLB is low, the lipophilic part predominates.

These emulsifiers preferably include polymeric emulsifiers, which are characterized by a high molar mass and a nonlinear structure which makes possible greater anchoring at the water/oil interface than that obtained with emulsifiers of monomer type.

The emulsifiers which can be used according to the invention, alone or as a mixture, are those which make it possible to produce inverse emulsions and which have an HLB of less than 7.

Generally, the preferred emulsifiers are silicone emulsifiers of organopolysiloxane type, such as:

E1) polyalkylmethicone copolyols (oxyalkylenated polyalkylmethylsiloxanes which are optionally crosslinked) comprising saturated or unsaturated and linear or branched $C_6$ to $C_{20}$ alkyl chains a polyoxyethylene unit having from 1 to 50 EO (ethylene oxide) groups and/or a polyoxypropylene unit having from 1 to 50 PO (propylene oxide) groups E2) oxyalkylenated polyalkyldimethylmethylsiloxanes comprising saturated or unsaturated and linear or branched $C_6$ to $C_{20}$ alkyl chains a polyoxyethylene unit having from 1 to 50 EO groups and/or a polyoxypropylene unit having from 1 to 50 PO groups.

The organopolysiloxanes of the compositions of the invention comprise in particular one or more oxyalkylene groups and in particular oxyethylene (EO) groups, for example from 1 to 40 oxyalkylene units, preferably from 1 to 20, better still from 10 to 20, more preferably from 12 to 20 and even better still from 12 to 18 oxyalkylene units, which can form polyoxyalkylene chains and in particular polyoxyethylene chains. These groups can be pendant or at the chain end. The silicon atoms carrying these groups advantageously number from approximately 1 to 10 and better still from 1 to 6. The silicone structure forming the polymeric backbone of the organopolysiloxane comprising oxyalkylene group(s) is advantageously a polydimethylsiloxane (PDMS) structure, a portion of the methyl groups of which is optionally replaced by $C_2$ to $C_{30}$, preferably $C_8$ to $C_{24}$ and better still $C_{10}$ to $C_{20}$ alkyl groups or phenyl groups, either at the chain end or pendant.

Advantageously employed as emulsifiers of E1 or E2 type, are silicone emulsifiers, such as alkyldimethicone copolyols, for example Abil EM-90, or the mixture of dimethicone copolyol and cyclomethicone marketed by Dow Corning under the trademark 3225C Formulation Aid, the laurylmethicone copolyol marketed under the trademark Emulsifier 10 by Dow Corning, or mixtures based on a silicone polymer, such as the cetyldimethicone copolyol with polyglyceryl-4 isostearate and hexyl laurate marketed under the trademark Abil WE09 by Goldschmidt, Abil EM 97 from Goldschmidt (dimethicone copolyol & cyclomethicone), Wacker SPG 128 VP from Wacker (cyclomethicone and octyldimethicone methoxy glycosyl), or Silwax WD-IS (dimethicone copolyol isostearate).

E3) siloxane mono- or polyalkyl esters, for example Silwax S from Lambent (dimethiconol stearate), E4) alkoxylated carboxylic acid esters, such as PEG polyhydroxylated alkyl esters, for example Arlacel P 135 from Uniqema (PEG-30 dipolyhydroxystearate).

Preferably employed are emulsifiers with an HLB of from 2 to 7, preferably a silicone W/O emulsifier with an HLB of from 2 to 7, preferably a polymeric silicone W/O emulsifier with an HLB of from 2 to 7.

The compositions according to the invention will in particular comprise, expressed as percentage by weight, from 0.5 to 8% of emulsifier, for example from 0.5 to 5%, preferably from 3 and 5%, with respect to the total weight of the composition.

The compositions according to the invention preferably comprises a silicone emulsifier selected from among laurylmethicone copolyol, cetyldimethicone copolyol, a mixture of dimethicone copolyol and cyclomethicone or a mixture of cetyldimethicone copolyol with polyglyceryl-4 isostearate and hexyl laurate.

Furthermore, advantageously, in order to improve the stability of the dispersion, it is possible to combine, with the main emulsifiers described above, one or more coemulsifiers having an HLB of greater than 6. The coemulsifier/emulsifier ratio will advantageously be less than 1.5 and preferably less than 0.75.

Exemplary thereof are:

sorbitan alkyl or polyalkyl esters which are or are not polyoxyethylenated, with from 1 and 5 saturated or unsaturated and linear or branched $C_{10}$ to $C_{20}$ alkyl chains and with from 0 to 40 EO groups (for example: sorbitan monolaurate 20 EO or sorbitan monooleate 20 EO (Tween 80 from Uniqema));

polyoxyethylenated alkyl or polyalkyl ethers or esters, with from 1 and 5 saturated or unsaturated and linear or branched $C_{10}$ to $C_{20}$ alkyl chains and with from 0 to 40 EO groups (ceteareth-20 (Eumulgin B2 from Cognis) or steareth (Brij 78) 20 EO);

ethoxylated and esterified alkyl or polyalkyl mono- or polyglucosides, with from 1 and 5 saturated or unsaturated and linear or branched $C_6$ to $C_{20}$ alkyl chains and from 1 to 10 glucose units (for example, PEG-20 methylglucose sesquistearate (Glucamate SSE-20 from Amerchol));

polyglycerol alkyl or polyalkyl esters or ethers, with from 1 to 5 saturated or unsaturated and linear or branched $C_{10}$ to $C_{20}$ alkyl chains and from 1 to 8 glycerol units (for example, polyglyceryl-4 isostearate or PEG-8 stearate (Myrj 45)).

Preferably, the compositions according to the invention also comprise a coemulsifier having an HLB of greater than 6 which is preferably ceteareth-20.

Finally, it is possible to advantageously add, to the dispersed phase, from 0.001 to 10% by weight, with respect to the total weight of the formulation, of a cosolvent for the active principle having an evaporation temperature of less than 100° C., preferably linear or branched $C_1$ to $C_4$ alcohols, such as ethanol and isopropanol.

Advantageously, the preparation of the emulsions according to the invention has proven to require only a small amount of mechanical or thermal energy, in comparison with the preparations of other inverse emulsions already known.

In known manner, the compositions of the invention can also comprise the adjuvants usual in the cosmetics and dermatological fields, such as hydrophilic or lipophilic gelling agents, humectants, such as glycerol and sorbitol, fatty-phase thickeners, preservatives, antioxidants, electrolytes, solvents, fragrances, fillers, screening agents, pigments, odor absorbers, coloring materials and metal-chelating agents. The amounts of these various adjuvants are those conventionally employed in the fields under consideration, for example from 0.01 to 20% of the total weight of the composition. These adjuvants, depending on their nature, can be introduced into the lipophilic phase or into the hydrophilic phase. These adjuvants, and their concentrations, must be such that they do not adversely affect the cosmetic and/or dermatological properties of the compositions according to the invention.

Exemplary are hydrophilic gelling agents, of carboxyvinyl polymers (carbomer), acrylic copolymers, such as acrylate/alkylacrylate copolymers or acrylate copolymers, polyacrylamides, polysaccharides, natural gums and clays, and mention may be made, as lipophilic gelling agents, of modified clays, such as bentones, metal salts of fatty acids, hydrophobic silica or silicone gums. Preferably, according to the invention, the following commercial gelling agents are employed:

Lubrajel, marketed by Guardian, which is a mixture of glyceryl polymethacrylate and of propylene glycol, Aculyn 44, marketed by Rohm and Haas, which is a mixture of PEG-150, of decyl alcohol and of SMDI copolymer.

The compositions according to the invention have a cosmetically acceptable feel, good skin tolerance and good physical stability, namely, absence of phase separation and maintenance of the size of the globules under cold conditions (at 4° C.) and under warm conditions (45° C.) over a long period of time, for example over 3 months, with a stable viscosity over this period. The compositions according to the invention also make it possible to confer, on the active principle, good chemical stability and to prevent it from crystallizing over time.

In particular, the present invention relates to cosmetic or dermatological compositions for topical application to the skin, superficial body growths and/or mucous membranes, in the form of inverse emulsions comprising a dispersed glycolic or aqueous/glycolic hydrophilic phase and a continuous lipophilic phase, the same comprising, in a physiologically acceptable medium (that is to say, compatible with topical application on the skin, superficial body growths and/or mucous membranes), expressed as percentage by weight with respect to the total weight of the composition:

from 0.01 to 5% of ivermectin,
from 30 to 70% of glycols,
from 0.5 to 8% of emulsifier with an HLB of from 2 to 7,
from 0 to 5% of coemulsifier with an HLB of greater than 6,
from 0 to 50% of water, preferably from 0 to 25% of water.

In a specific embodiment of the invention, the dispersed hydrophilic phase has a water activity of less than 0.85.

The compositions according to the invention are useful medicaments.

The present invention also features formulating the subject compositions into medicaments useful to prevent and/or treat dermatological conditions selected from rosacea, acne vulgaris, seborrheic dermatitis, perioral dermatitis, acneiform eruptions, transient acantholytic dermatosis and acne miliaris necrotica.

The subject compositions formulated as inverse emulsions and preferably comprising ivermectin are more particularly useful for the treatment of rosacea, whether regime or regimen.

This invention also features pharmaceutical preparations and the medicaments obtained therefrom.

In order to further illustrate the present invention and the advantages thereof, the following specific examples are given, it being understood that same are intended only as illustrative and in nowise limitative. In said examples to follow, all parts and percentages are given by weight, unless otherwise indicated.

Example 1

Methods of Preparation of the Compositions of Examples 2 and 3 According to the Invention In the compositions below (Examples 2 to 3), the proportions of the various constituents are expressed as percentages by weight, unless otherwise indicated.

The compositions of Examples 2 and 3 are prepared in the following manner:

Fatty Phase A:

The constituents of fatty phase A are weighed out and heated to 55° C.

Phase B:

The ivermectin is dissolved in propylene glycol heated to 55° C.

The other constituents are incorporated.

Preemulsification:

Phase B is slowly introduced into fatty phase A with moderate stirring.

Cooling:

The mixture is maintained under stirring until it reaches ambient temperature.

Phase C:

The electrolyte is dissolved in the water.

Phase D (if applicable):

Phase D is added to phase C.

Emulsification:

The aqueous phase (C+D) is slowly introduced into the preemulsion with moderate stirring.

Example 2

Composition

| Phase A | |
|---|---|
| Laurylmethicone copolyol | 3.00% |
| Cyclopentasiloxane | 6.00% |
| Mineral oil | 15.00% |
| Butylated hydroxytoluene | 0.10% |
| Phase B | |
| Propylene glycol | q.s. for 100% |
| Glyceryl polymethacrylate (and) propylene glycol | 5.00% |
| Ivermectin | 1.00% |
| Phase C | |
| Purified water | 20.00% |
| Magnesium sulfate heptahydrate | 1.00% |

Example 3

Composition

| Phase A | |
|---|---|
| Laurylmethicone copolyol | 3.00% |
| Cyclopentasiloxane | 6.00% |
| Mineral oil | 10.00% |
| Butylated hydroxytoluene | 0.10% |
| Phase B | |
| Propylene glycol | q.s. for 100% |
| Glyceryl polymethacrylate (and) propylene glycol | 5.00% |
| Ivermectin | 1.00% |
| Phase C | |
| Purified water | 14.00% |
| Magnesium sulfate heptahydrate | 1.00% |
| Phase D | |
| Ethanol, Rectapur | 5.00% |

Example 4

Stability Results for the Composition According to Example 2

Physical Stability:

The physical stability of the formulations is measured by macroscopic and microscopic observation of the formulation at ambient temperature, at 4° C., at 40° C. and at 55° C. after 1, 2, 3, indeed even 6 and 9 months.

At ambient temperature (AT), macroscopic observation makes it possible to guarantee the physical integrity of the products and microscopic observation makes it possible to confirm that the dissolved active principle has not recrystallized.

At 4° C., microscopic observation confirms that the dissolved active principles have not recrystallized.

At 40° C. and/or at 55° C., macroscopic observation confirms the integrity of the finished product.

Specifications at $T_0$, at AT, of the Composition According to Example 2:

Macroscopic appearance: thick colorless or very slightly yellow milk.

Microscopic appearance: size of the ivermectin globules from 2.5 μm and 12.5 μm.

| Stability conditions | Time | | |
|---|---|---|---|
| | T 1 M | T 2 M | T 3 M |
| AT | Conforms to the specifications | Conforms to the specifications | Conforms to the specifications |
| +4° C. | Conforms to the specifications | Globules of 2.5 μm to 25 μm | Globules of 2.5 μm to 25 μm |
| +55° C. | Conforms to the specifications | Globules of 2.5 μm to 25 μm | Globules of 2.5 μm to 25 μm |

Measurements of the viscosity (τ=shear stress):

| | | |
|---|---|---|
| $T_{initial}$ ($T_0$): | at 4 s$^{-1}$, τ = 34 Pa | at 20 s$^{-1}$, τ = 87 Pa |
| $T_{3\ months}$/AT: | at 4 s$^{-1}$, τ = 33 Pa | at 20 s$^{-1}$, τ = 75 Pa |
| $T_{3\ months}$/40° C.: | at 4 s$^{-1}$, τ = 36 Pa | at 20 s$^{-1}$, τ = 81 Pa |

These results show very good reproducibility and excellent stability over 3 months of the rheological profile of the formulation according to the invention.

b) Chemical Stability of the Active Principle within the Composition According to Example 2:

The active principle is quantitatively determined by HPLC with internal calibration.

| | AT | 40° C. |
|---|---|---|
| $T_0$ | 97.7% | |
| $T_{1\ month}$ | 97.8% | 97.9% |
| $T_{2\ months}$ | 99.2% | 98.5% |
| $T_{3\ months}$ | 99.2% | 98.4% |
| $T_{6\ months}$ | 99.1% | 98.6% |

These results show that the active principle within the composition and the composition itself are highly stable.

Example 5

Stability Results for the Composition According to Example 3

Physical Stability:
Specifications at $T_0$, at AT, of the Composition According to Example 3
Macroscopic appearance: soft colorless or very slightly yellow cream.
Microscopic appearance: size of the ivermectin globules from 2.5 μm and 12.5 μm.

| Stability conditions | Time | | |
|---|---|---|---|
| | T 1 M | T 2 M | T 3 M |
| AT | Conforms to the specifications | Conforms to the specifications | Conforms to the specifications |
| +4° C. | Conforms to the specifications | Globules of 2.5 μm to 25 μm | Globules of 2.5 μm to 25 μm |
| +55° C. | Conforms to the specifications | Globules of 2.5 μm to 25 μm | Globules of 2.5 μm to 25 μm | c) Chemical Stability of the Active Principle within the Composition According to Example 3
The active principle is quantitatively determined by HPLC with internal calibration.

| | AT | 40° C. |
|---|---|---|
| $T_0$ | 100.7% | / |
| $T_{1\ month}$ | 100.7% | 101.1% |
| $T_{2\ months}$ | 101.4% | 102.6% |
| $T_{3\ months}$ | 101.0% | 107.9% |
| $T_{6\ months}$ | 101.0% | 98.6% |
| $T_{9\ months}$ | 98.4% | / |
| $T_{12\ months}$ | 97.9% | / |

These results show that the active principle within the composition and the composition itself are highly stable.

Example 6

Evaluation of the Tolerance of the Composition According to Example 2 by a Test of Local Tolerance after Repeated Application in Mice The goal of the present study is to compare the irritant power of the placebo composition with various ivermectin placebo compositions.
The treatment consists of a daily topical application of a composition on the internal face of the right ear of BALB/c mice for 6 days.
The products to be tested are:
Group 1: Cream formula A
Group 2: Cream formula B
Group 3: Cream gel formula C
Group 4: Gel formula D
Group 5: Emulsion E
Group 6: Inverse emulsion according to the invention F
Evaluation is carried out by measurements of the thickness of the ear using the Oditest and by clinical observation of the animals from the $2^{nd}$ to the $12^{th}$ day.

The results are:

| | AUC for edema D2-D19 | | % AUC inhibition | | Student's t-test vs |
|---|---|---|---|---|---|
| | Mean | SEM | vs Differin | p values | untreated |
| Untreated | 209.4 | 1.8 | | | |
| Group 1: Cream formula A | 238.5 | 2.8 | 13.9 | 0.0000 | *** |
| Group 2: Cream formula B | 243.5 | 4.4 | 16.3 | 0.0001 | *** |
| Group 3: Cream gel formula C | 227 | 5.8 | 8.4 | 0.206 | * |
| Group 4: Gel formula D | 306.1 | 6.7 | 46.2 | 0.0000 | *** |
| Group 5: Emulsion E | 228.6 | 2.5 | 9.2 | 0.0002 | *** |
| Group 6: Inverse emulsion according to the invention F | 208.8 | 2.4 | −0.3 | 0.8473 | NS |

The formulations according to the invention do not bring about an increase in the thickness of the ear. Such formulations are thus regarded as very well tolerated in mice and significantly different from the other compositions tested.

Each patent, patent application, publication, text and literature article/report cited or indicated herein is hereby expressly incorporated by reference in its entirety.

While the invention has been described in terms of various specific and preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A cosmetic/dermatological composition which comprises an inverse emulsion of a glycolic or aqueous/glycolic hydrophilic phase dispersed in a continuous lipophilic phase, said inverse emulsion comprising, as percentages by weight with respect to the total weight thereof, ivermectin in an amount of from 0.01% to 5%, glycols in an amount of from 30% to 70%, an emulsifier having an HLB ranging from 2 to less than 7 in an amount of from 0.5% to 8%, water in an amount of up to 25% and, optionally, a coemulsifier having an HLB of greater than 6 in an amount of up to 5%, said inverse emulsion being physically and chemically stable and oxidation-resistant.

2. The cosmetic/dermatological composition as defined by claim 1, devoid of DHEA and/or vitamin D derivative.

3. The cosmetic/dermatological composition as defined by claim 1, said ivermectin being dissolved in the dispersed glycolic or aqueous/glycolic phase.

4. The cosmetic/dermatological composition as defined by claim 2, comprising about 1% of ivermectin.

5. The cosmetic/dermatological composition as defined by claim 1, said emulsifier having an HLB ranging from 2 to less than 7 comprising a silicone emulsifier.

6. The cosmetic/dermatological composition as defined by claim 1, said emulsifier having an HLB ranging from 2 to less than 7 being selected from the group consisting of laurylmethicone copolyol, cetyldimethicone copolyol, a mixture of dimethicone copolyol and cyclomethicone, and a mixture of cetyldimethicone copolyol with polyglyceryl-4 isostearate and hexyl laurate.

7. The cosmetic/dermatological composition as defined by claim 1, wherein the coemulsifier having an HLB of greater than 6 is present.

8. The cosmetic/dermatological composition as defined by claim 7, wherein said coemulsifier comprises ceteareth-20.

9. The cosmetic/dermatological composition as defined by claim 1, wherein the proportion by volume of glycol, with respect to the total volume of the dispersed phase, ranges from 60% to 100%.

10. The cosmetic/dermatological composition as defined by claim 1, wherein the dispersed phase comprises at least one glycol selected from the group consisting of propylene glycol, hexylene glycol, dipropylene glycol and PEG 400.

11. The cosmetic/dermatological composition as defined by claim 1, formulated as a medicament.

12. A method for the treatment of rosacea, comprising administering to an individual in need of such treatment, a thus effective amount of the cosmetic/dermatological composition as defined by claim 1.

13. The cosmetic/dermatological composition as defined by claim 1, further comprising an adjuvant selected from the group consisting hydrophilic gelling agents, lipophilic gelling agents, humectants, fatty-phase thickeners, preservatives, antioxidants, electrolytes, solvents, fragrances, filters, screening agents, pigments, odor absorbers, coloring materials and metal-chelating agents.

14. The cosmetic/dermatological composition as defined by claim 1, further comprising an electrolyte.

15. The cosmetic/dermatological composition as defined by claim 14, wherein the electrolyte is magnesium sulfate heptahydrate.

* * * * *